(12) United States Patent
Harper et al.

(10) Patent No.: US 10,610,447 B2
(45) Date of Patent: Apr. 7, 2020

(54) DEVICE, SYSTEM AND METHOD FOR FACILITATING BREATHING VIA SIMULATION OF LIMB MOVEMENT

(71) Applicant: The Regents of the University of California, Oakland, CA (US)

(72) Inventors: Ronald M. Harper, Los Angeles, CA (US); Mary Ann Woo, Los Angeles, CA (US); Sergey Shaboyan, Los Angeles, CA (US); Paul Macey, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 678 days.

(21) Appl. No.: 14/906,684

(22) PCT Filed: Jul. 22, 2014

(86) PCT No.: PCT/US2014/047642
§ 371 (c)(1),
(2) Date: Jan. 21, 2016

(87) PCT Pub. No.: WO2015/013293
PCT Pub. Date: Jan. 29, 2015

(65) Prior Publication Data
US 2016/0158097 A1 Jun. 9, 2016

Related U.S. Application Data

(60) Provisional application No. 61/856,883, filed on Jul. 22, 2013.

(51) Int. Cl.
*A61H 23/00* (2006.01)
*A61H 23/04* (2006.01)
(Continued)

(52) U.S. Cl.
CPC ............... *A61H 23/04* (2013.01); *A61F 5/56* (2013.01); *A61H 23/02* (2013.01); *A61H 31/00* (2013.01);
(Continued)

(58) Field of Classification Search
CPC ...... A61H 23/04; A61H 39/007; A61H 23/02; A61H 31/00; A61H 16/00;
(Continued)

(56) References Cited

U.S. PATENT DOCUMENTS 3,082,414 A * 3/1963 Papaminas ............. B60K 28/06
128/903
4,297,685 A * 10/1981 Brainard, II ............. A61B 5/01
340/573.1
(Continued)

OTHER PUBLICATIONS

Eldridge et al. "Stimulation by Central Command of Locomotion, Respiration and Circulation During Exercise." Respir Physiol 1985; 59:313-337.
(Continued)

*Primary Examiner* — Steven O Douglas
(74) *Attorney, Agent, or Firm* — Riverside Law LLP

(57) ABSTRACT

A device, system and method for increasing air intake by a subject is described. The device includes a vibration motor and a control unit for controlling vibrational motion output by the vibration motor. The methods include positioning the vibration motor on one or more limbs of a subject, and stimulating nerves in the limbs via the generated vibrational motion, whereby the stimulated nerve signals the brain to increase breathing rate or air intake by the subject. Accordingly, embodiments of the device activate nerve fibers that carry kinesthetic cues from the limbs in a pattern that simulates normal limb motion, and thus triggers inherent reflexes that increase ventilation in response to such motion.

20 Claims, 19 Drawing Sheets

(51) Int. Cl.
*A61F 5/56* (2006.01)
*A61H 39/00* (2006.01)
*A61H 31/00* (2006.01)
*A61M 16/00* (2006.01)
*A61H 23/02* (2006.01)

(52) U.S. Cl.
CPC ........... *A61H 39/007* (2013.01); *A61M 16/00* (2013.01); *A61H 2201/164* (2013.01); *A61H 2201/165* (2013.01); *A61H 2201/1635* (2013.01); *A61H 2201/501* (2013.01); *A61H 2201/5002* (2013.01); *A61H 2201/5005* (2013.01); *A61H 2201/5038* (2013.01); *A61H 2201/5097* (2013.01); *A61M 2205/056* (2013.01); *A61M 2205/332* (2013.01); *A61M 2205/3569* (2013.01); *A61M 2205/3592* (2013.01); *A61M 2205/8206* (2013.01); *A61M 2210/08* (2013.01); *A61M 2230/42* (2013.01)

(58) Field of Classification Search
CPC .... A61H 2201/5097; A61H 2201/1635; A61H 2201/5038; A61H 2201/501; A61H 2201/5005; A61H 2201/5002; A61H 2201/165; A61H 2201/164; A61F 5/56; A61M 2205/332; A61M 2205/056; A61M 2205/3569; A61M 2205/8206; A61M 2230/42; A61M 2210/08
See application file for complete search history.

(56) References Cited

U.S. PATENT DOCUMENTS

| | | | | |
|---|---|---|---|---|
| 6,445,303 | B1* | 9/2002 | Aryeh | G08B 21/06 180/272 |
| 6,935,335 | B1* | 8/2005 | Lehrman | A61B 5/0002 128/200.24 |
| 8,140,164 | B2 | 3/2012 | Tehrani et al. | |
| 9,318,013 | B2* | 4/2016 | Zohar | G08B 21/06 |
| 9,830,783 | B1* | 11/2017 | Kessler | G08B 6/00 |
| 2003/0199945 | A1 | 10/2003 | Ciulla | |
| 2007/0255330 | A1 | 11/2007 | Lee et al. | |
| 2010/0057154 | A1 | 3/2010 | Dietrich et al. | |
| 2010/0249637 | A1 | 9/2010 | Walter et al. | |
| 2011/0282164 | A1 | 11/2011 | Yang et al. | |
| 2014/0111340 | A1 | 4/2014 | Zohar | |

OTHER PUBLICATIONS

Fink et al. "Hyperpnoea during and immediately after exercise in man: evidence of motor cortical involvement" J. Physiol 1995; 489 (pt 3):663-675.

Iscoe and Polosa "Synchronization of respiratory frequency by somatic afferent stimulation" J. Appl Physiol, 1976; vol. 40: 138-148.

Potts et al. "Respiratory Rhythm Entrainment by Somatic Afferent Stimulation" J Neurosci, 2005; vol. 25(8): 1965-1978.

Pan et al. "Independence of exercise hyperpnea and acidosis during high-intensity exercise in ponies" J Appl Physiol 1986; 60: 1016-1024.

Paton et al. "Ventilatory Response to Exercise in Children with Congenital Central Hypoventilation Syndrome" The Am Rev Respir Dis 1993; vol. 147:1185-1191.

Gozal et al. "Ventilatory Responses to Passive Leg Motion in Children with Congenital Central Hypoventilation Syndrome" Am J Respir Crit Car Med, 1996; vol. 153:761-768.

Gozal and Simakajornboon "Passive Motion of the Extremities Modifies Alveolar Ventilation during Sleep in Patients with Congenital Central Hypoventilation Syndrome" Am J Respir Crit Car Med, 2000; vol. 162:1747-1751.

Harper et al. "Neural responses to paced breathing in congenital central hypoventilation syndrome" Society for Neuroscience Abstracts 2005, 352.1.

Macey et al. "Functional magnetic resonance imaging during passive foot movement in congenital central hypoventilation syndrome patients" Society for Neuroscience Abstracts 2005, 635.13.

\* cited by examiner

Respiratory Analysis
Subject 1

Night 1

| | Number (Index) |
|---|---|
| Obstructive | 3 (1.6) |
| Mixed | - |
| Central | - |
| Undef A. | - |
| Total A. | 3 (1.6) |
| Hypopnoea | 125 (65.8) |
| A+H | 128 (67.4) |
| Limitation | - |
| RERAs | - |
| RDI | 128 (67.4) |

Night 2 (Stim)

| | Number (Index) |
|---|---|
| Obstructive | - |
| Mixed | - |
| Central | - |
| Undef A. | - |
| Total A. | - |
| Hypopnoea | 63 (17.4) |
| A+H | 63 (17.4) |
| Limitation | - |
| RERAs | 3 (0.8) |
| RDI | 66 (18.2) |

Figure 12A

Respiratory Analysis
Subject 2

Night 1

| | Number (Index) |
|---|---|
| Obstructive | 25 (4.2) |
| Mixed | 2 (0.3) |
| Central | 28 (4.7) |
| Undef A. | - |
| Total A. | 55 (9.2) |
| Hypopnoea | 84 (14.1) |
| A+H | 139 (23.3) |
| Limitation | - |
| RERAs | - |
| RDI | 139 (23.3) |

Night 2 (Stim)

| | Number (Index) |
|---|---|
| Obstructive | 1 (0.1) |
| Mixed | - |
| Central | 1 (0.1) |
| Undef A. | - |
| Total A. | 2 (0.3) |
| Hypopnoea | 40 (6.0) |
| A+H | 42 (6.3) |
| Limitation | - |
| RERAs | - |
| RDI | 42 (6.3) |

Figure 12B

DEVICE, SYSTEM AND METHOD FOR FACILITATING BREATHING VIA SIMULATION OF LIMB MOVEMENT

CROSS-REFERENCE TO RELATED APPLICATIONS

This application the U.S. national phase application filed under 35 U.S.C. § 371 claiming benefit to International Patent Application PCT/US14/47642, filed Jul. 22, 2014, which is entitled to priority under 35 U.S.C. § 119(e) to U.S. Provisional Patent Application No. 61/856,883, filed on Jul. 22, 2013, the contents of which are incorporated by reference herein in its entirety.

BACKGROUND OF THE INVENTION

Multiple respiratory conditions lead to inadequate air intake in subjects to meet their metabolic needs, resulting in an increased level of carbon dioxide or decreased oxygenation in the body. The conditions include obstruction of the upper airway during sleep, periodic cessation of breathing movements interspersed with breathing efforts, and reduced excitation of the respiratory musculature from spinal cord injury or impaired brain processes Typical interventions to assist breathing in patients with such impaired breathing patterns include positive pressure ventilation via forced air through a face mask or via a tracheostomy, or negative pressure ventilation through a sealed chamber, such as an "iron lung." Positive pressure ventilation through a face mask is unpleasant, remodels the boney facial structure in developing children, and is often rejected by patients after a short period of use for reasons of discomfort. A tracheostomy poses serious infection concerns. Iron lungs restrict movement, since the lower body is encased in a chamber, and must be carefully regulated to avoid obstructive sleep apnea.

Other interventions include direct electrical stimulation of the phrenic nerve which serves the diaphragm, a procedure which requires highly invasive surgery, together with a potential for phrenic nerve injury. A risk also exists for a failure of the phrenic stimulating leads post-surgery, which can potentially have fatal consequences. Experimental procedures are being investigated to assist breathing by electrical or magnetic stimulation of the spinal cord, but those procedures are not in clinical use.

Thus, there is a need in the art for alternative, non-invasive, devices and procedures that are easy to use for assisting a subject's breathing or air intake. The present invention satisfies this need.

SUMMARY OF THE INVENTION

A device, system and method for enhancing air intake by a subject are described. The device includes a vibration motor and a control unit for controlling vibrational motion output by the vibration motor. The methods include positioning the vibration motor on at least one limb of a subject, and stimulating a nerve in the limb via the generated vibrational motion, whereby the stimulated nerve signals the brain to increase air intake by the subject. Accordingly, the device of the present invention activates proprioceptive nerve fibers that carry kinesthetic cues from the limbs in a pattern that simulates normal limb motion.

In one embodiment, the at least one limb is the subject's leg. In another embodiment, the at least one limb is the subject's arm. In another embodiment, the stimulated nerve is the ulnar nerve of the arm. In one embodiment, the at least one vibrator is controlled by a control unit. In another embodiment, the control unit is programmable. In one embodiment, the control unit is programmable via a computing device that is wired or wirelessly connected to the control unit. In another embodiment, the control unit controls the vibration motor wirelessly. In another embodiment, the device and method may be used while the subject is sleeping. In one embodiment, the subject has a condition selected from the group consisting of hypoventilation, obstructive sleep apnea, heart failure, central sleep apnea, apnea of prematurity, apnea of infancy, muscular dystrophy, spinal cord injury, and stroke.

In one embodiment, the method comprises the delivery of pulses at rate of about 20-70 pulses per minute. In one embodiment, the vibrator is programmed to vary inputs such as pulse rate, pulse duration interpulse duration, burst duration, interburst duration, and pulse amplitude. In another embodiment, the vibration motor is programmed to pulse in a variable-amplitude sequence. In another embodiment, the vibration motor is between 2-15 mm in diameter. In another embodiment, the vibration motor is embedded in a material attached to the subject's limb. In another embodiment, the vibration motor is positioned against the skin surface of the subject's limb and is covered by a material attached to the subject's limb.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 12, comprising FIG. 12A-FIG. 12C, depicts the results of an experiment examining the effect of limb stimulation on the respiration of subjects. The respiratory analysis of two subjects (FIG. 12A and FIG. 12B) demonstrate that stimulation facilitates the breathing in each subject. FIG. 12C demonstrates that stimulation reduces respiratory disturbance index (RDI) in each subject.

FIG. 13, comprising In FIG. 13A, the sustained periods of waking when the subject should be sleeping was reduced in Night 2. In FIG. 13B, stimulation induced much longer periods of rapid eye movement sleep (REM sleep) in the second night with stimulation.

FIG. 14, comprising FIG. 14A: Respiratory tracings (airflow) from Pre (Baseline), Stimulation on hand, and Post Stimulation periods from a 2 year old congenital central hypoventilation patient under clinical intervention. FIG. 14B: Peak-to-trough amplitude of airflow, and index of air exchange, in Pre (Baseline), Stimulation of hand, and Post Stimulation periods in arbitrary units. FIG. 14C: Respiratory rate in Baseline, Stimulation, and Post Stimulation periods. Stimulation significantly enhanced amplitude, without changing the respiratory rate.

DETAILED DESCRIPTION

Figure 1:
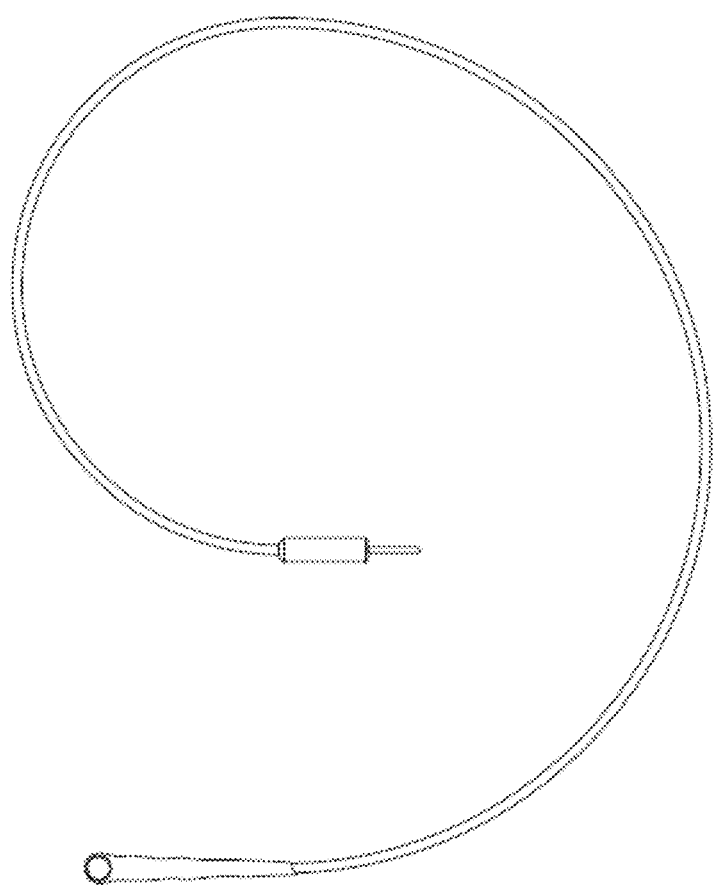
FIG. 1 is an image of an exemplary circular vibratory device attached to insulated wires from a control unit.

It is to be understood that the figures and descriptions of the present invention have been simplified to illustrate elements that are relevant for a clear understanding of the present invention, while eliminating, for the purpose of clarity, many other elements found in typical assisted breathing devices and techniques. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

Throughout this disclosure, various aspects of the invention can be presented in a range format. It should be understood that the description in range format is merely for convenience and brevity, and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, 6 and any whole and partial increments therebetween. This applies regardless of the breadth of the range.

The present invention is based in part on the discovery that vibrational stimulation of proprioceptor fibers of the limb of a subject enhances breathing. The coupling of breathing with limb motion reaches back to observations made of breathing patterns in race horses on cold days when synchronization of expired breath with leg movements could be noted, and has since been documented in a large number of physiological studies in both animals and humans (Eldridge et al., 1985, Respir Physiol, 59: 313-337; Fink et al, 1995, J Physiol, 489 (Pt 3): 663-675; Iscoe and Polosa, 1976, J Appl Physiol, 40: 138-148; Potts et al., 2005, J Neurosci, 25: 1965-1978). Effects of limb motion are independent from carbon dioxide drive (Pan et al., 1986, J Appl Physiol, 60: 1016-1024), an extremely important aspect in cases where, through genetic or other injury, brain structures which mediate carbon dioxide drive are damaged, and that drive is missing. This aspect is a special concern in cases of congenital hypoventilation syndrome, where such patients are unresponsive to carbon dioxide and fail to breathe during sleep. Even quiescent behavior, such as watching television, often results in hypoventilation and life-threatening falls in oxygenation in these patients.

However, it has been observed that such children may increase ventilation with active exercise, such as when playing soccer (Paton et al., 1993, The Am Rev Respir Dis 147: 1185-1191). Cyclic movement of the feet in affected children increases breathing (Gozal et al., 1996, Am J Respir Crit Car Med, 153: 761-768), and that relationship is maintained even during sleep (Gozal and Simakajornboon, 2000, Am J Respir Crit Car Med, 162: 1747-1751). The means by which that coupling between limb movement and breathing occurs has been explored with functional magnetic resonance imaging, and demonstrates the integration of the limb and respiratory musculature systems (Harper et al., 2005, Society for Neuroscience Abstracts, 352.1). Unfortunately, provoking such limb movement during sleep, or even during waking hours, is often impractical.

Thus, the present invention includes a system and device to simulate signals from the limbs that are interpreted by the brain as movement, and through coupling of those signals with activity in respiratory-related brain areas, elicit enhanced breathing efforts or rate by the subject. Since walking or running is not feasible during sleep or other daily activities, the present invention can be used to activate a subject's brain areas governing breathing that use the neural activity normally generated with such limb movement.

In certain embodiments, the present invention facilitates breathing in a subject suffering from hypoventilation via stimulation of a region of at least one of the subject's limbs. For example, in certain aspects the invention provides stimulation of proprioceptive afferent fibers located for example at the back of the knee, palm of the hand, back of the elbow, wrist, and the like. For example, the invention may stimulate fibers in one or more toes, feet, ankles, legs, fingers, arms, wrists, or hands. Stimulation will increase breathing rate in both normal subjects and subjects with hypoventilation, but is much more effective in subjects with hypoventilation.

The device of the present invention activates nerve fibers that carry kinesthetic cues from the limbs in a pattern that simulates normal limb motion. As contemplated herein, the device includes a mechanical vibrator and a programmable control unit that controls the vibrator. The present invention is unique in that stimulation of the subject is unrelated to carbon dioxide stimulation, positive pressure ventilation, and electrical stimulation of the respiratory system. Unlike these existing techniques, the present invention instead incorporates non-invasive neural processes to provide increases in ventilation to improve oxygen delivery to tissue.

The device of the present invention uses a vibratory device to activate the same sensory nerves as those carrying signals indicating foot movement, thus signaling the brain to increase respiratory rate without requiring increased carbon dioxide stimulation normally needed to increase breathing rate.

For example, as shown in FIG. 1, the mechanical vibrator may be a small, circular vibrator with a diameter of approximately 7 mm. Preferably, the vibration motor is between about 2-15 mm in size to localize the vibration stimulus to the underlying nerve fibers. However, it should be appreciated that the vibration motor may be of any type, size or dimension as understood by those skilled in the art, provided the vibrator is capable of neural stimulation, as described herein.

Figure 2C:
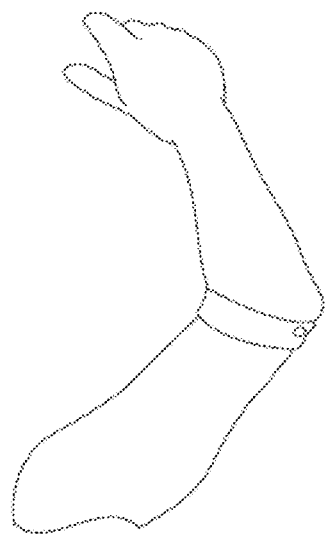
FIGS. 2A-2C illustrate exemplary positioning of the vibrator over primary sensory fibers from the joints and muscles of a subject's legs (FIG. 2A), arms (FIG. 2C) or wrists (FIG. 2B).
Figure 2B:
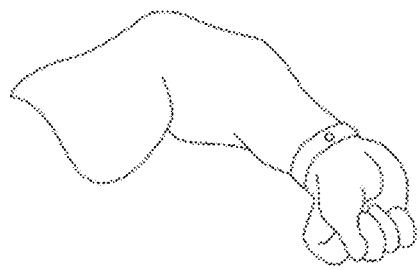
Figure 2A:
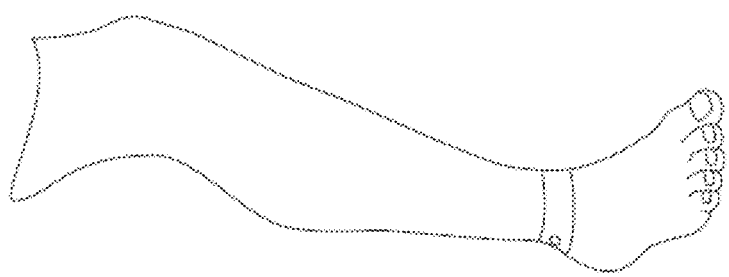
Figure 3A:
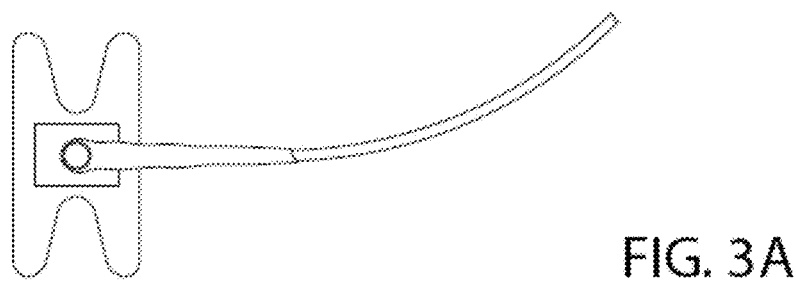
FIG. 3A illustrates a vibrator secured to an adhesive bandage.
Figure 3B:
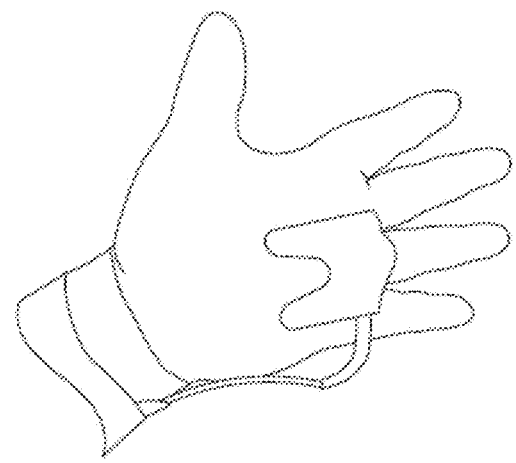
FIGS. 3B and 3C illustrate alternate views positioning of the vibrator on the hand using the bandage.
Figure 3C:
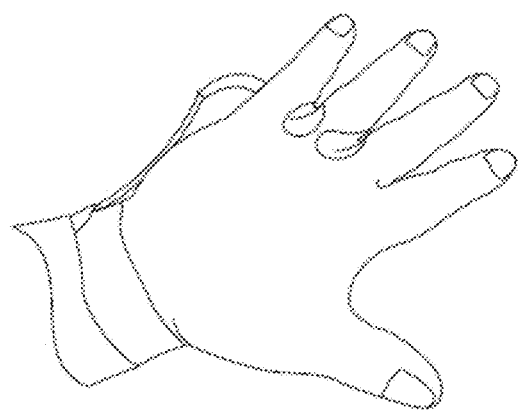

As contemplated herein, the vibrational stimulator may be placed on at least one region of the subject's limb. In some embodiments, a single vibrator is positioned on a limb for neural stimulation, and in other embodiments, multiple vibrators are positioned on one or more limbs for neural stimulation. For example, one or more vibrators may be positioned on one or more toes, feet, ankles, legs, fingers, arms, wrists, or hands of a subject being treated. The vibrator may be placed on the surface skin overlying sensory nerves which normally carry signals on limb motion, to stimulate the nerves through mechanical vibration at rates which mimic patterns of activity found during limb activity accompanying movement. In one embodiment, the vibrator is placed directly onto the subject's skin surface, for example on the surface of the skin of the ankle overlying the tibial nerve. In another embodiment, at least one layer of fabric, polymer or other material is placed between the subject's skin surface and the vibrator. In another embodiment, the vibrator is embedded in a material, such as a fabric or an elastic material such as neoprene or other polymer. For example, as shown in FIG. 2, the vibrator may be placed over primary sensory fibers from the joints and muscles of the subject's feet, legs, arms or hands, and secured into position via an elastic bandage or a wrapping, such as a Velcro wrap, to maintain position. As shown in FIG. 2A, a Velcro band may include an embedded vibrator overlying a sensory nerve carrying kinesthetic sensation from the foot and ankle to simulate movement during walking. Vibrators can also be placed above the knee to stimulate nerves carrying sensory information from that joint. As shown in FIG. 2B, the vibrator can be placed over sensory nerves within the wrist, or as shown in FIG. 2C, the vibrator can be placed over the ulnar nerve of the arm near the elbow to stimulate nerves simulating arm movement. Such upper limb placements may be favorable for subjects with spinal cord injury, where sensory nerve information from the lower limbs may be lost; these patients often require assistance in breathing, especially during sleep, since innervation to abdominal respiratory muscles is often diminished. In certain embodiments, the vibrator is placed on the hand or palm of a subject (FIG. 3). For example, as depicted in FIG. 3A, the vibrator may be secured to an adhesive bandage. The bandage can then be applied to a suitable position on the hand or palm of the subject (FIG. 3B and FIG. 3C). Optionally, the present invention may further include a device to open a subject's airway to facilitate breathing. Non-limiting examples of such devices include mouthpieces or oral appliances commonly used for treatment of snoring or sleep apnea.

Figure 4A:
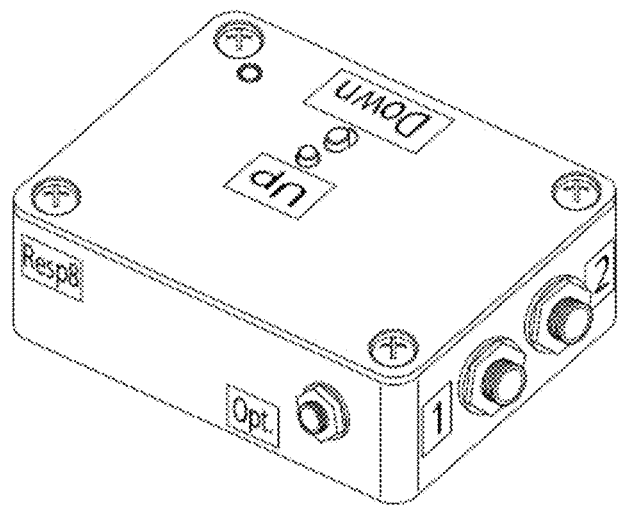
FIGS. 4A and 4B illustrate alternate perspective views of an exemplary control unit of the system.
Figure 4B:
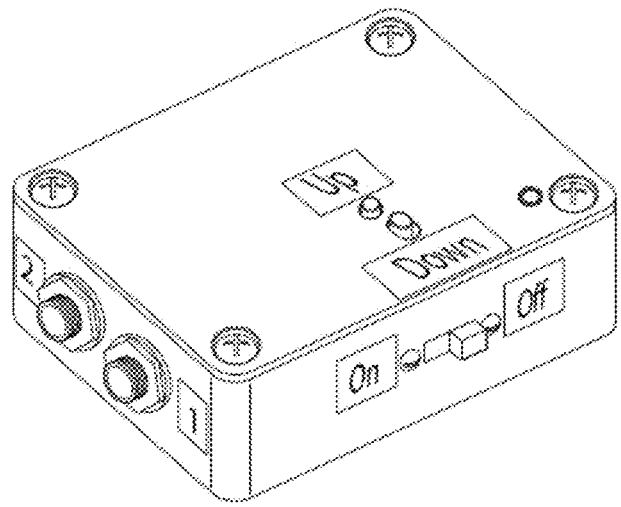
Figure 5:
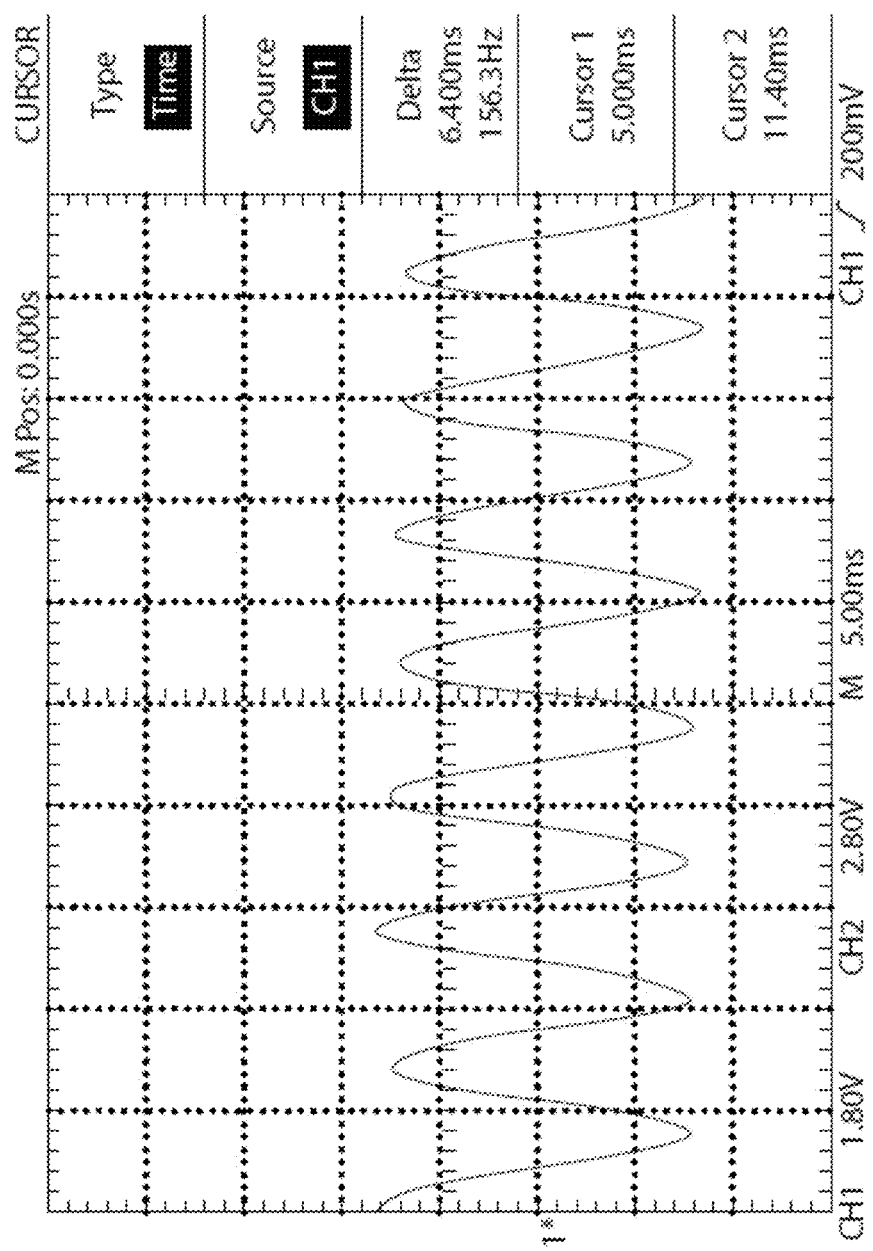
FIG. 5 is an illustration of the waveform of mechanical vibration emitted by an exemplary control unit.

As shown in FIG. 4, the vibrator is controlled by a programmable control unit to induce vibrations. For example, the vibrator may be switch-programmed to pulse in a variable-amplitude sequence that evokes nerve fiber discharge similar to that arising from walking or running. As contemplated herein, the control unit may be programmed to vary the pulse rate, pulse interval, duration of pulses, duration of pulse-burst interval, and pulse amplitude (to increase or decrease force of the vibrator) as desired, such that the delivered vibrational energy is capable of neural stimulation, as described herein.

The pulse rates are established to mimic signals from moving limbs matching a rate of movement found to be effective in increasing respiratory rate in normal children and children with congenital central hypoventilation syndrome (Macey et al., 2005, Society for Neuroscience Abstracts 635.13). However, the rates may change with age, since mimicking extension and flexion of the leg will change as the rate of walking slows with age.

For example, in certain embodiments, the device is programmed to deliver one or more set of pulses, via the vibrator, to the subject. For example, in one embodiment, the device delivers a continuous train of pulses for a defined period.

In one embodiment, the pulses are delivered at rate of about 1-200 pulses per minute. In one embodiment, the pulses are delivered at rate of about 10-100 pulses per minute. In one embodiment, the pulses are delivered at rate of about 20-70 pulses per minute. In one embodiment, the pulses are delivered at rate of about 62 pulses per minute.

In one embodiment, each pulse is delivered at about 10-1000 Hz. In one embodiment, each pulse is delivered at about 100-500 Hz. In one embodiment, each pulse is delivered at about 152 Hz.

In one embodiment, the duration of each individual pulse, (i.e., pulse duration) is about 0.01-60 seconds. In one embodiment, the pulse duration is about 0.1-10 seconds. In one embodiment, the pulse duration is about 0.2-1 seconds. In one embodiment, the pulse duration is about 0.4 seconds.

In one embodiment, the duration between successive pulses (i.e., inter-pulse duration) is about 0.01-60 seconds. In one embodiment, the inter-pulse duration is about 0.1-10 seconds. In one embodiment, the inter-pulse duration is about 0.2-1 seconds. In one embodiment, the inter-pulse duration is about 0.4 seconds.

In one embodiment, the total time period where the pulses are delivered, including pulse duration and interpulse duration, is about 1 second-1000 minutes. In one embodiment, the total time period where the pulses are delivered is about 1-500 minutes. In one embodiment, the total time period where the pulses are delivered is about 5-100 minutes.

In certain embodiments, the device delivers one or more sets or bursts of pulses, where each burst comprises one or more pulses and where each burst is separated by an inter-burst interval. For example, in one embodiment, the device delivers a plurality of bursts, where each burst comprises a pulse train, and where each burst is separated by an inter-burst interval.

In one embodiment, the duration of each burst is about 1 second-1000 minutes. In one embodiment, the duration of each burst is about 1-500 minutes. In one embodiment, the duration of each burst is about 5-100 minutes.

In one embodiment, the duration of the inter-burst interval is about 1 second-1000 minutes. In one embodiment, the duration of the inter-burst interval is about 1-500 minutes. In one embodiment, duration of the inter-burst interval is about 5-100 minutes.

In certain embodiments, the entire stimulation protocol, including for example a continuous train of pulses or a plurality of bursts of pulses, is repeated as suitable over minutes, hours, days, and the like.

The parameters of the stimulation, including for example, pulse duration, burst duration, interpulse interval, interburst interval, and may vary substantially to meet the needs for activating upper airway muscles over those of the diaphragm, or for particular breathing conditions where more rapid or slower respiratory efforts are desired. Specific stimulation paradigms for various conditions are described elsewhere herein.

The amplitude of the pulses from the vibration unit can be set by the programming device, and can be set to maximal displacement to account for individuals with excessive fat or tissue over the nerve fibers, or to lower levels in cases where very little tissue separates the surface of the skin from the nerve fibers. Pulse amplitudes may be set lower to avoid arousals during sleep states where excessive vibration may lead to unnecessary wakenings. In certain embodiments, the device may provide a range of amplitudes in the range of about 0-2 G (vibrational force), where G is gravitational acceleration, and equals 9.8 m/s$^2$. In certain embodiments, the device is controlled by the user to control the particular amount of vibrational force needed or desired.

Figure 6:
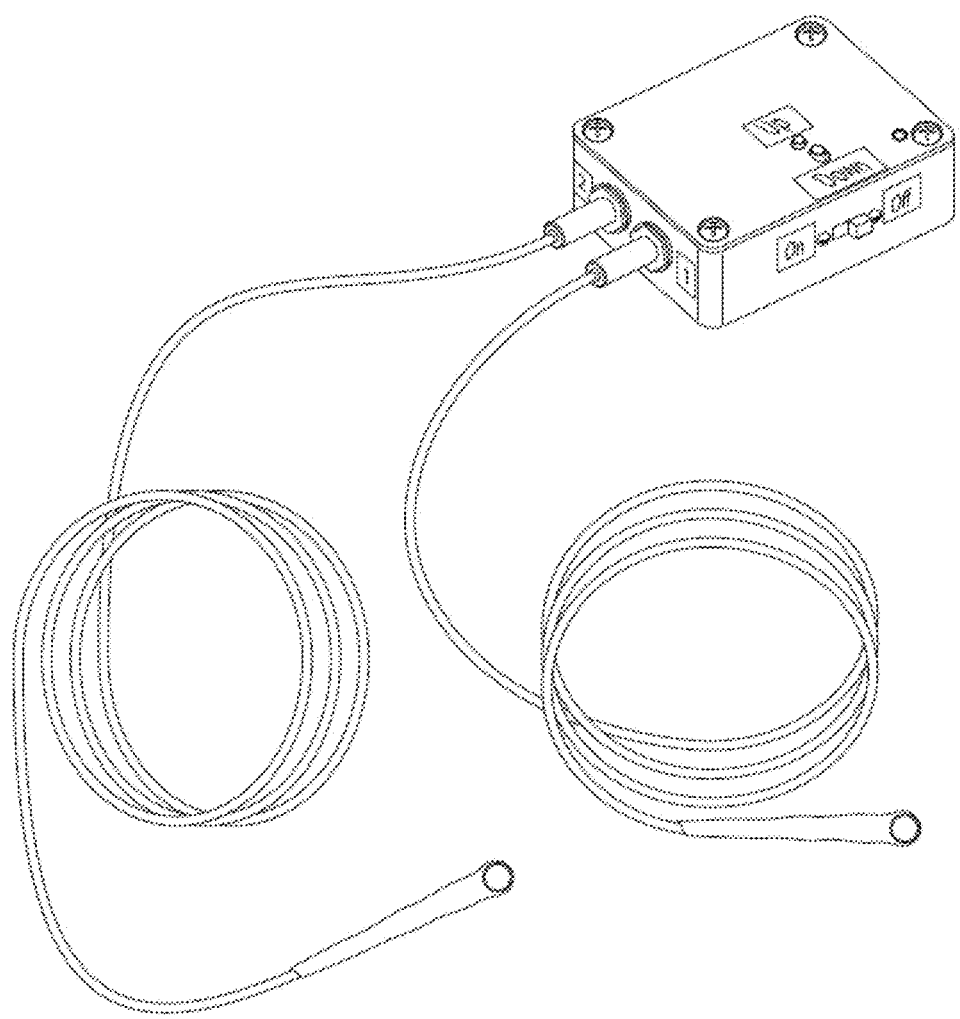
FIG. 6 is an image of an exemplary vibrator component attached to the control unit via insulated wires and connector.

In one embodiment, the programmable control unit is battery powered. For example, in one embodiment, the control unit comprises a 9V battery. In certain embodiments, the battery is rechargeable. For example, in certain aspects the battery may be wirelessly recharged using components and techniques known in the art. In one embodiment, the programmable control unit comprises an isolated plug for accessing electricity from a home, hospital or other location providing access to an electrical power source. In one embodiment, the control unit is electrically connected to the vibrator via an electrical lead, cable or wire, as shown in FIG. 6. For example, the device may comprise one or more leads carrying low DC voltage to the vibrator. In one embodiment, the control unit comprises multiple outputs for communication with multiple individual vibrators. For example, the control unit may communicate with two or more different vibrators, delivering the same or different stimulation parameters to the two or more vibrators. In other embodiments, the vibrator includes a wireless receiver and a power source so that the vibrator component may receive signals from the control unit wirelessly. In one embodiment, the control unit comprises a memory device to store different stimulation protocols, user data, and the like.

In one embodiment, the control unit may include a user interface including a display screen to provide text or other graphics indicating user information, such as stimulation parameters of amplitude, duration, intervals, battery power level, and the like. The user interface may also include one or more depressible buttons, dials, recessed switches or a touch screen through which the control unit may be programmed by a user.

Figure 7:
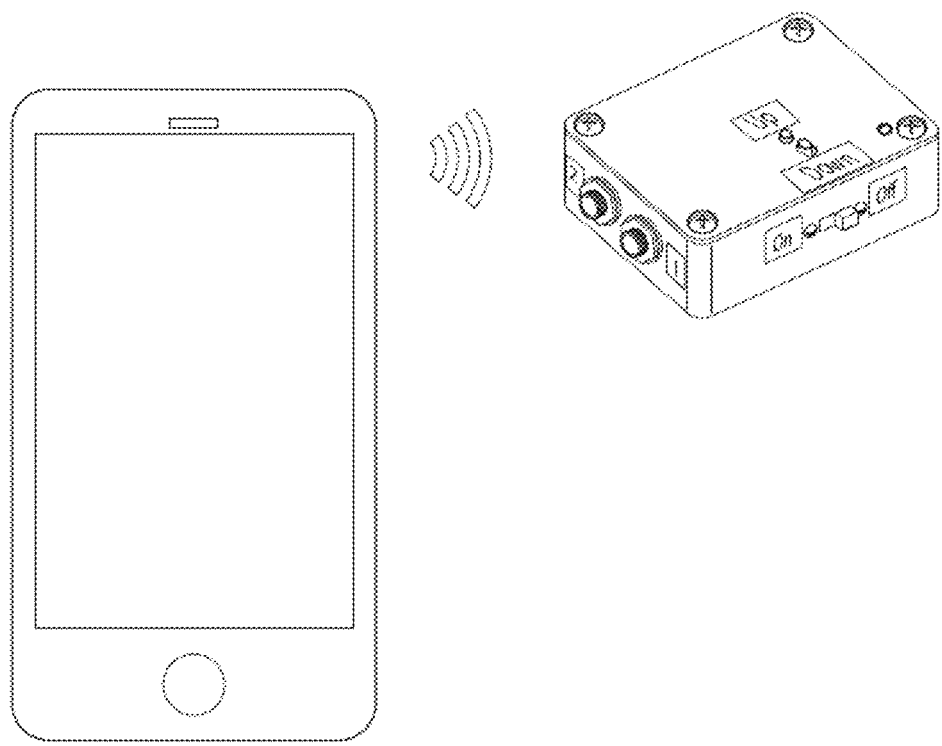
FIG. 7 is an image of an exemplary stimulation device that is programmed externally by a wireless smartphone or tablet through Bluetooth means. The programming characteristics of the pulse sequences are set through the external computing device.

In one embodiment, the programmable control unit or vibrator receives stimulation parameters via a computing device, such as a computer, laptop, smartphone, tablet, watch, television, or the like (FIG. 7). For example, the device of the invention may be controlled directly by a wireless computing device, such as tablets, smartphones or other wireless digital/cellular devices that are Bluetooth or network enabled, and includes a software application platform or portal providing a user interface as contemplated herein. The computing devices may include at least one processor, standard input and output devices, as well as all hardware and software typically found on computing devices for storing data and running programs, and for sending and receiving data over a network. In certain embodiments, the computing device comprises a display suitable for visual representation of system control and status. The communications between the computing device and the control unit or vibrator may be conducted via any wireless based technology, including, but not limited to radio signals, near field communication systems, hypersonic signal, infrared systems, cellular signals, GSM, and the like.

In certain embodiments, the computing device comprises a software application used for the input of stimulation parameters, delivery of stimulation parameters, storage of stimulation protocols, storage of user information, and the like. The software application platform may be a local or remotely executable software platform, or a hosted internet or network program or portal.

The software platform includes a graphical user interface (GUI) for inputting stimulation parameters, modulating function of the control unit and vibrator, and for displaying information regarding the historical or real-time functionality of the device, as well as historical or real-time functionality of the subject's respiratory activity. In certain embodiments, wireless communication for information transfer to and from the computing device may be via a wide area network and may form part of any suitable networked system understood by those having ordinary skill in the art for communication of data to additional computing devices, such as, for example, an open, wide area network (e.g., the internet), an electronic network, an optical network, a wireless network, personal area networks such as Bluetooth, a physically secure network or virtual private network, and any combinations thereof. Such an expanded network may also include any intermediate nodes, such as gateways, routers, bridges, internet service provider networks, public-switched telephone networks, proxy servers, firewalls, and the like, such that the network may be suitable for the transmission of information items and other data throughout the system.

As would be understood by those skilled in the art, the computing device may be wirelessly connected to the expanded network through, for example, a wireless modem, wireless router, wireless bridge, and the like. Additionally, the software platform of the system may utilize any conventional operating platform or combination of platforms (Windows, Mac OS, Unix, Linux, Android, etc.) and may utilize any conventional networking and communications software as would be understood by those skilled in the art.

To protect data, an encryption standard may be used to protect files from unauthorized interception over the network. Any encryption standard or authentication method as may be understood by those having ordinary skill in the art may be used at any point in the system of the present invention. For example, encryption may be accomplished by encrypting an output file by using a Secure Socket Layer (SSL) with dual key encryption. Additionally, the system may limit data manipulation, or information access. Access or use restrictions may be implemented for users at any level. Such restrictions may include, for example, the assignment of user names and passwords that allow the use of the present invention, or the selection of one or more data types that the subservient user is allowed to view or manipulate.

In certain embodiments the network provides for telemetric data transfer to and from the control unit, vibrator, and computing device. For example, data transfer can be made via any wireless communication technology, including, but not limited to radio signals, near field communication systems, hypersonic signal, infrared systems, cellular signals, GSM, and the like. In some embodiments, data transfer is conducted without the use of a specific network. Rather, in certain embodiments, data are directly transferred to and from the control unit and computing device via systems described above.

The software may include a software framework or architecture that optimizes ease of use of at least one existing software platform, and that may also extend the capabilities of at least one existing software platform. The software provides applications accessible to one or more users (e.g. patient, clinician, etc.) to perform one or more functions. Such applications may be available at the same location as the user, or at a location remote from the user. Each application may provide a graphical user interface (GUI) for ease of interaction by the user with information resident in the system. Exemplary GUIs of the invention are provided in FIG. 8-FIG. 10, which depict the ability for a user to control and monitor the stimulation parameters of the device. A GUI may be specific to a user, set of users, or type of user, or may be the same for all users or a selected subset of users. The system software may also provide a master GUI set that allows a user to select or interact with GUIs of one or more other applications, or that allows a user to simultaneously access a variety of information otherwise available through any portion of the system. Presentation of data through the software may be in any sort and number of selectable formats. For example, a multi-layer format may be used, wherein additional information is available by viewing successively lower layers of presented information. Such layers may be made available by the use of drop down menus, tabbed pseudo manila folder files, or other layering techniques understood by those skilled in the art.

The software may also include standard reporting mechanisms, such as generating a printable results report, or an electronic results report that can be transmitted to any communicatively connected computing device, such as a generated email message or file attachment. Likewise, particular results of the aforementioned system can trigger an alert signal, such as the generation of an alert email, text or phone call, to alert a patient, doctor, nurse, emergency medical technicians, or other health care provider of the particular results.

Figure 8:
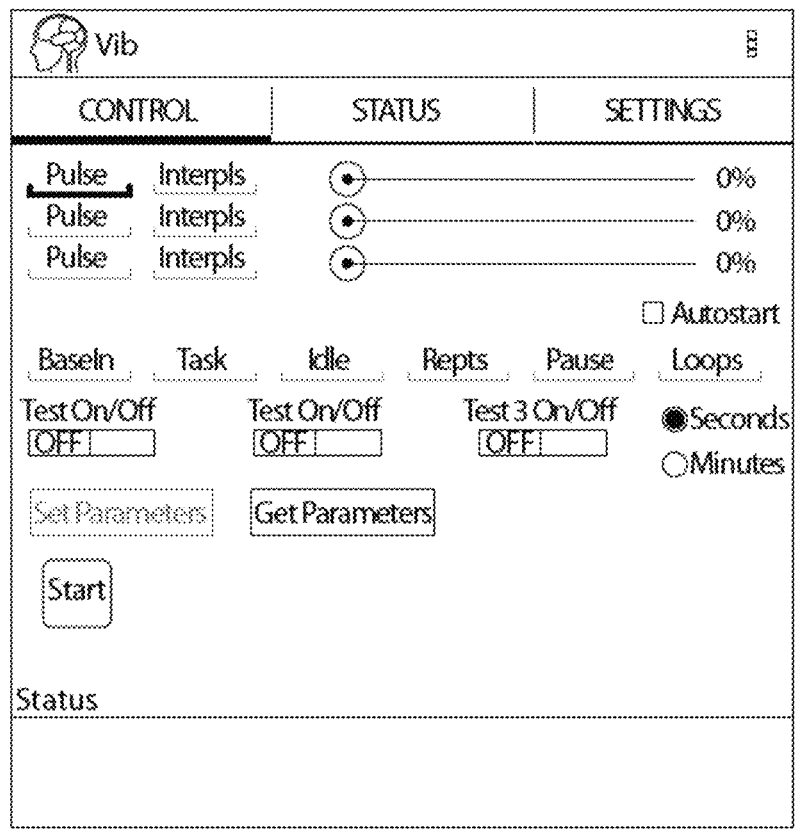
FIG. 8 is an image of an exemplary graphical user interface (GUI) of a software application on an external computing device which is used to input and control stimulation parameters to be delivered to the control unit and vibrator.
Figure 9:
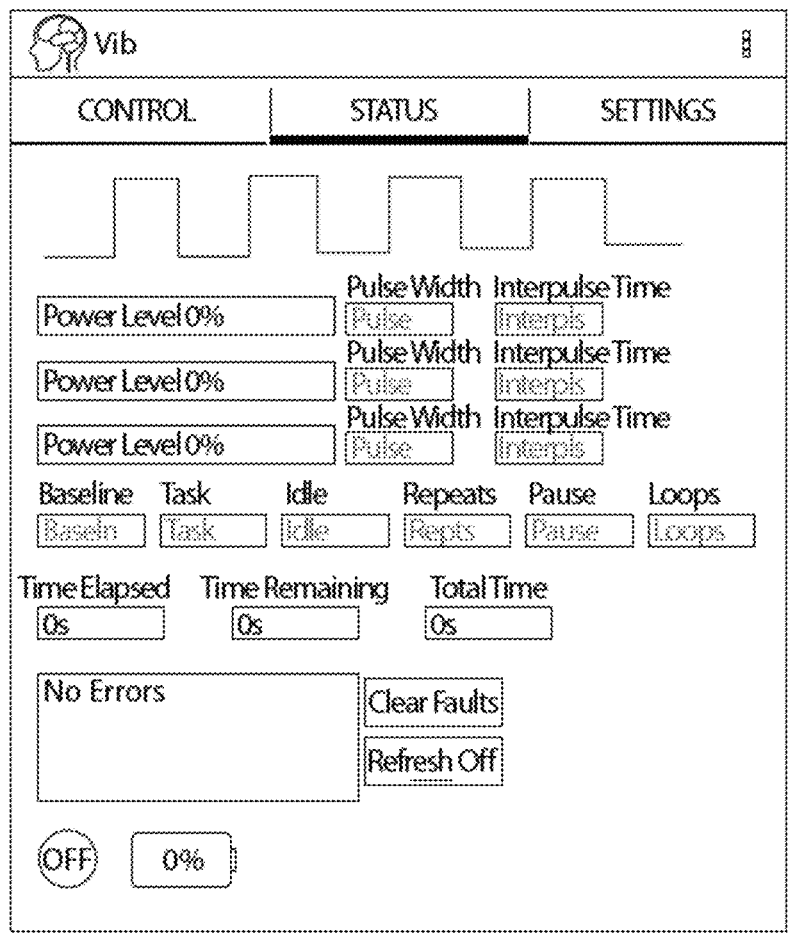
FIG. 9 is an image of an exemplary graphical user interface (GUI) of a software application on an external computing device which is used to provide feedback from the control unit and vibrator to the user, and to monitor the current parameters set in the control unit.
Figure 10:
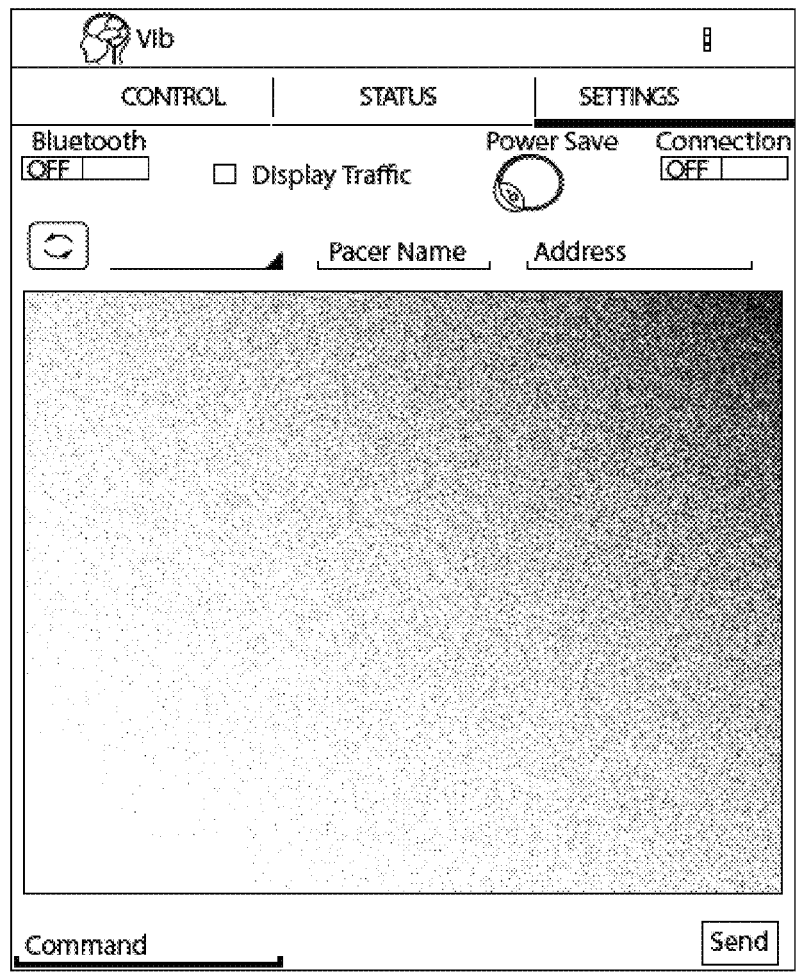
FIG. 10 is an image of an exemplary graphical user interface (GUI) of a software application on an external computing device which is used to monitor and change connection settings of the computing device to the control unit or vibrator.

Exemplary GUIs of the system of the present invention are depicted in FIG. 8-FIG. 10. For example, in one embodiment, the software comprises a control layer, status layer, a settings layer, and menu layer. In one embodiment, each layer is accessible by a user to allow for control and/or observation of data relating to the selected layer. Upon selection by a user, each layer provides a unique GUI that allows for interaction with the layer. Layers may be selected using tabs, drop down menus, and other strategies known in the art. For example, in certain embodiments, the computing device and software allow for touch-sensitive interaction, where the GUIs of the system are interacted with via touch of the display. In certain embodiments, the GUIs of the system are interacted with using standard computing hardware, including, but not limited to, a keyboard, mouse, and the like.

In one embodiment, the software of the system comprises a control layer and a control GUI. The control GUI comprises tools to control pulse characteristics (FIG. 8). For example, the GUI comprises text fields, drop down menus, sliders, buttons, and the like which allow a user to input stimulation parameters, as described elsewhere herein. The control GUI allows for input of, for example, pulse duration, interpulse duration, pulse amplitude, and the like, for multiple connected vibrators, thereby allowing for independent control of each vibrator being implemented. In certain embodiments, the control GUI allows for input of the baseline duration (time between start of procedure and onset of vibration), task period (duration of vibration period including inter-pulse intervals), the idle period (the idle time between successive vibration or task periods), and the number of repeats (the total number of repeated vibration or task periods). In certain embodiments, the control GUI allows for input of the amplitude levels of vibration of each vibrator. For example, an entire period may include a baseline period of 30 sec before vibration starts, a 300 sec task period, 30 sec idle time between the next 300 sec period, with each 300 sec period being repeated 5 times, thereby providing five stimulation periods of 5 minutes per period. In one embodiment, the control GUI provides an option for sending the inputted parameters to the control unit. Further, the control GUI provides a Start/Stop button to initiate stimulation based upon the inputted parameters. The control GUI may also allow for directly turning the vibrators on or off, either for testing or for treatment purposes. In certain embodiments, the control GUI allows the user to save one or more parameters which can then be loaded for future use.

In one embodiment, the software of the system comprises a status layer and a status GUI. The status GUI is designed to provide feedback from the control unit and/or vibrator to the user, and to monitor the current parameters set in the control unit (FIG. 9). For example, the status GUI may comprise fields that indicate the pulse width, interpulse time, baseline duration, task period, idle period, and number of repeats set in the control unit. Further, in certain embodiments the status GUI displays the set vibration power level for each vibrator, where "power level" indicates the vibrational amplitude, expressed in percentage of maximum possible amplitude. In certain embodiments, the status GUI comprises one or more fields indicating the elapsed time, time remaining, and total time of a stimulation protocol. In one embodiment, the status GUI comprises a field displaying the number of faults detected and/or registered by the control unit. In one embodiment, the status GUI comprises a button for clearing of the fault memory. In certain embodiments, the status GUI comprises one or more indicators of the on/off state of each vibrator and the battery state of the control unit. In one embodiment, the status GUI comprises a refresh toggle or switch that allows the user to select whether the parameters of the status GUI auto refreshes at a defined refresh interval (e.g., every half second). In one embodiment, the status GUI displays a graph to indicate the overall stimulation protocol as well as the current position, in time, of the stimulation process.

In one embodiment, the software of the system comprises a settings layer and a settings GUI. The settings GUI allows the user to monitor and change connection settings of the computing device to the control unit and/or vibrator (FIG. 10). For example, the settings GUI provides options for controlling the Bluetooth or wireless settings of the system. In one embodiment, the settings GUI comprises a switch that allows the user to enable and disable communication to and from the computing device. For example, the switch may turn off the Bluetooth or wireless communication of the computing device. In one embodiment, the settings GUI comprises a switch to establish a connection (e.g., a Bluetooth connection or wireless connection) to the control unit and/or vibrator of the system. For example, if the communication of the computing device is enabled, a user can then establish communication to the control unit and/or vibrator. In certain embodiments, the settings GUI comprises a list of available devices which may be selected in order to establish connection. In one embodiment, connection to a device is made by manually entering the name, MAC address, or other identifying feature of the device. In one embodiment, the settings GUI comprises a refresh button to allow the user to refresh a list of recently-paired or nearby devices. In one embodiment, the settings GUI comprises a power saving switch that allows the user to enable the power saving mode of the system. For example, a power saving mode disconnects the control unit and vibrator from the computing device and renders the control unit and/or vibrator in a power saving state while remained in a powered state. The settings GUI may comprise a display traffic switch that enables display of all incoming and outgoing data. In certain embodiments, the settings GUI comprises one or more fields for sending a message or command to the connected device.

In one embodiment, the software of the system comprises a menu layer and a menu GUI. In one embodiment, the menu GUI allows a user to save the currently set stimulation parameters in the control unit or in the computing device. In one embodiment, the menu GUI comprises an option for exiting the software.

The present invention provides a method for facilitating breathing in a subject in need thereof. For example, the method may stimulate breathing to enhance sleep-disordered breathing. However, the method may also be used to assist compromised breathing in wakefulness.

Sleep-disordered breathing can generally be categorized into several breathing patterns, each of those patterns associated with different diseases. These patterns are now briefly described.

Hypoventilation

The term "hypoventilation" is a general phrase, referring to a broad range of inadequate ventilation from a number of potential sources. One source is that from neuromuscular diseases, such as Muscular Dystrophy, characterized by widespread muscle weakness, resulting in obstructive sleep apnea or insufficient muscle action to ensure adequate gas exchange. Spinal cord injury below cervical levels can result in impaired motoneuron outflow to thoracic and abdominal respiratory musculature, reducing ventilation. Enhanced airway resistance, or Upper Airway Resistance Syndrome results from a range of processes that resemble obstructive sleep apnea. The condition typically can only be detected with esophageal balloons or specialized sound devices, and leads to impaired ventilation and a range of cardiovascular consequences. The present invention can assist in all of these conditions, by further exciting upper airway muscles in patients with increased airway resistance, by recruiting more effort from weakened muscles of muscular dystrophy cases, and by providing additional neural drive to thoracic and abdominal musculature in spinal cord patients.

Figure 12C:
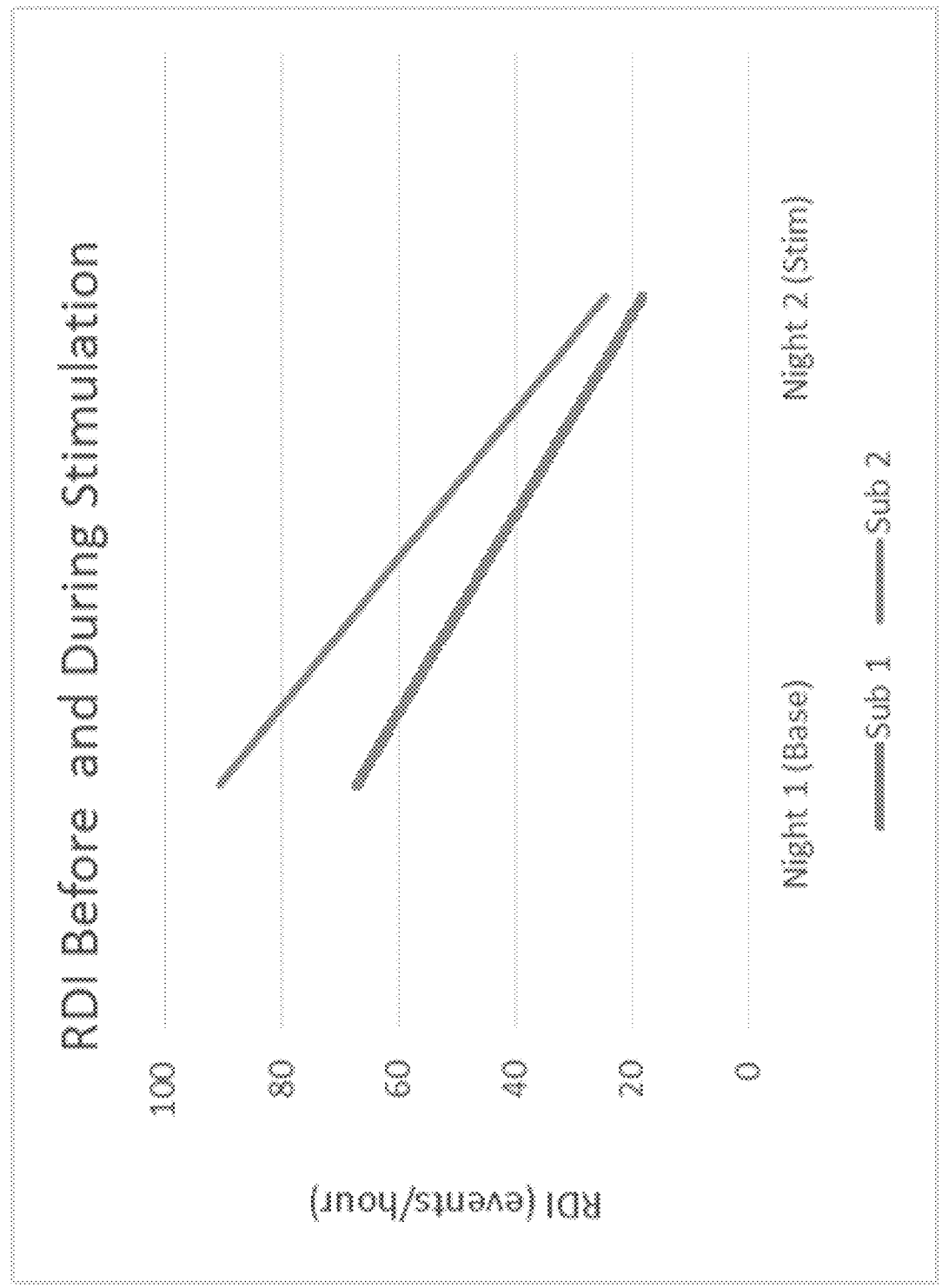

In one embodiment, the present invention may be used to facilitate breathing in a subject diagnosed with hypoventilation or respiratory depression. In certain embodiments, the present invention may be used to facilitate breathing in a subject having polio, congenital central hypoventilation syndrome (CCHS), muscular dystrophy, chronic obstructive pulmonary disease, spinal cord injury, injury to brain stem and high cervical spinal cord areas, genetic conditions which damage structures mediating sensitivity of brain areas to carbon dioxide drives to breathing, or even heart failure. Assistance for spinal cord and muscular dystrophy cases may be especially necessary during sleep, but ventilation during wakefulness is also a concern. In another embodiment, the present invention may be used to facilitate breathing in an infant suffering from apnea of prematurity. Such apnea typically consists of periodic breathing, i.e., patterns of no respiratory action (silence) interspersed with respiratory movements. Vibration intervention will facilitate action of respiratory muscles during those silent periods. In still other embodiments, the present invention may be used to facilitate breathing in a subject desiring more consistent or enhanced air intake for recovering muscles, such for use by an athlete resting after a rigorous workout. Examples of enhancing ventilation in spinal cord patients are shown in FIG. 12A-FIG. 12C, and the resulting improvement in sleep state integrity in FIG. 13A and FIG. 13B. Examples of enhancing ventilation in a child with congenital central hypoventilation is shown in FIG. 14.

Obstructive Sleep Apnea (OSA)

OSA is characterized by the collapse of the upper airway from inaction of upper airway respiratory muscles (e.g., genioglossal fibers of the tongue) with continued diaphragmatic efforts. The condition arises from loss of central neural coordination of drive to the upper airway muscles from phrenic nerve discharge to the diaphragm and spinal nerve activation of the thoracic wall/abdominal musculature. The blockade of the airway is now often treated by use of devices such as oral appliances commonly used for treatment of snoring or sleep apnea, or forcing air through an oral or nasal mask to dilate the upper airway, normally accomplished by continuous positive airway pressure (CPAP) devices, or devices to force air triggered to the inspiratory cycle of breathing.

The condition is defined as a separate entity, but accompanies a range of other conditions which exacerbate, and perhaps contribute to the initial development of OSA. These conditions include obesity, nasal obstruction by septal deviation sinusitis, nasal polyps chronic rhinitis, stenosis, or issues which contribute reduction of oral size, including enlarged tonsils/adenoids, hypothyroidism, and micrognathia. Strokes (especially cerebellar strokes), and menopause development (reduction in respiratory drive hormones, alterations in cervical column and oral airway) can also contribute. OSA also frequently accompanies Down's syndrome, Sickle Cell Anemia, heart failure, Alzheimer's Disease, epilepsy, and Cystic Fibrosis.

Figure 15:
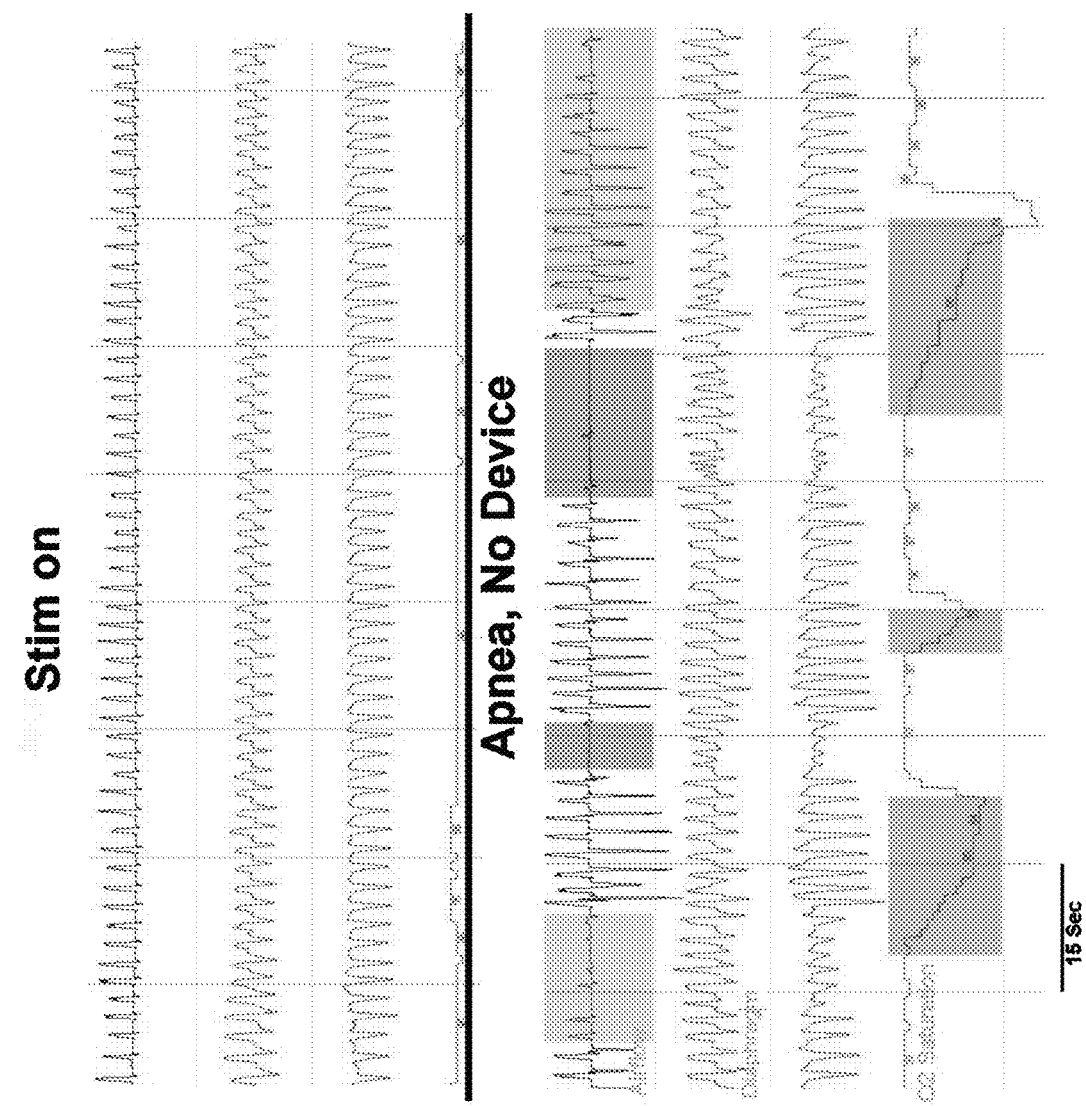
FIG. 15 illustrates the breathing patterns of a subject with obstructive sleep apnea with (Stim On) and without (Apnea, No Device) limb stimulation. The data demonstrates that, without the device, there is a series of obstructive events that reduces airflow and oxygen saturation. However, during stimulation, the breathing pattern of the subject is much improved.

The system and method of the present invention can assist breathing in OSA by recruiting upper airway muscles in a timely fashion to dilate the upper airway by activating upper airway musculature just prior to diaphragmatic descent. That is, the invention promotes the opening the airway so that negative pressure from the diaphragm will not collapse the soft upper airway tissue. For example, it has been demonstrated from functional magnetic resonance imaging studies, that activation of the proprioceptors by passive foot movement activates portions of the brain involved in exciting upper airway musculature as well as the diaphragmatic musculature (Harper et al., 2005, Society for Neuroscience Abstracts 352.1; Macey et al., 2005, Society for Neuroscience Abstracts 635.13). These studies provide evidence that the present invention would be useful in facilitate breathing in a subject with OSA. In preliminary studies, the device has reduced the incidence of apnea in an OSA subject by a factor of four. Further, as shown in FIG. 15, limb stimulation of a subject with OSA enhances the breathing patterns of the subject. It is shown that, without the device, there is a series of obstructive events that reduces airflow and oxygen saturation. However, during stimulation, the breathing pattern of the subject is much improved.

Central Apnea

Central apnea is a failure of the brain to provide sufficient "drive" to activate any of the respiratory musculature, resulting in inadequate intake of oxygen and exhalation of carbon dioxide. Central apnea can result from congenital disorders, such as mutation of PHOX2b, resulting in congenital central hypoventilation syndrome, or brain injury resulting from strokes, trauma, hemorrhage, or drug action, damage of the cervical spinal cord at levels C3, C4, or C5, and also appears in apnea of infancy, although such apnea is often periodic (described below). The present invention may be used to facilitate breathing in a subject with central apnea, as numerous studies have demonstrated improved ventilation with passive limb movement in congenital central hypoventilation, clinical use in recovery from apnea by passive foot stimulation in neonates, and improved breathing with rocking of infants.

Periodic and Cheyne-Stokes Breathing

Periodic breathing, found in apnea of infancy, drug action, and breathing at altitude, and Cheyne-Stokes breathing, a more severe form of periodic breathing, which occurs in conditions such as heart failure, and is a significant characteristic of the latter condition, result from a loss of coordination of ventilation-significant incoming signals of $CO_2$ and $O_2$ from the periphery (due to altered perfusion and other aspects), and central drive to breathing, arising from descending thermal and other forebrain drives and central chemoreceptors. The pattern is characterized by a succession of breaths, typically arising in a crescendo pattern, and then declining, followed by a loss of all respiratory effort, and repeated with another succession of breaths. The failure is one of coordination loss, which can be assisted by overriding the chemoreceptor signals from the significant proprioceptive drive of the device and method of the invention.

One example of a stimulation pattern that has been demonstrated to improve breathing during sleep in spinal cord patients was a continuous train of pulse durations of 0.4 sec, inter-pulse duration of 0.4 sec, task time 460 min, idle time 0, repeats 1. Another example of a stimulation pattern for obstructive sleep apnea comprised of bursts of trains with pulse durations of 0.1 sec, inter-pulse time 0.1 sec, burst duration of 2 sec, interburst duration of 2 sec, task time, 230 min, repeats 1. The specific stimulation pattern will vary with subject age and condition.

Subjects with congenital central hypoventilation syndrome benefit more from a pattern of vibration over proprioceptor fibers that simulate the burst-pause pattern of proprioceptor nerves responding to extending and flexing the limb during walking. Thus, a pulse duration of 1.0 sec, interpulse duration of 1.0 sec, with a task duration of 460 min, adequate for an all-night recording, would simulate the nerve pattern of discharge accompanying normal walking of an adult; the pulse duration and interpulse duration would be correspondingly shorter in a child, or if increased ventilation corresponding to running would be desired. The amplitude of vibration would normally be fixed at levels sufficient to stimulate the nerves underling the skin. However those levels may vary, depending on the skin thickness in adults over children or infants.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

Example 1: Limb Stimulation in Subjects with Congenital Central Hypoventilation (CCHS)

Figure 11:
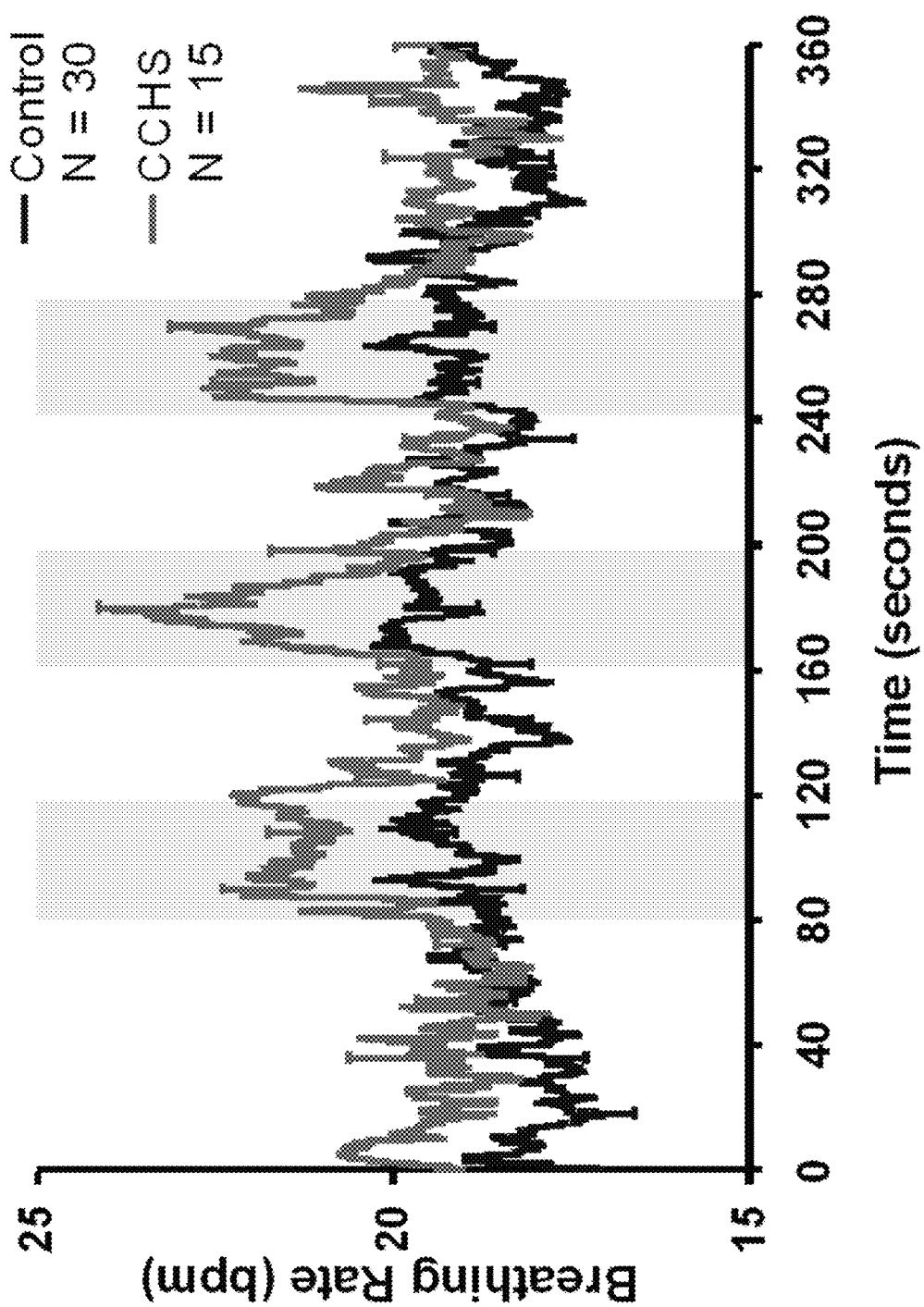
FIG. 11 is a graph showing the increase in breathing rate accompanying three periods of foot movement (indicated by shaded areas) in 30 normal subjects (control) and 15 children with congenital central hypoventilation (CCHS), illustrating the effect on breathing with movement that activates proprioceptor fibers of the foot. It is shown that even passive movement will elicit the change in breathing, not just subject-induced movement. It is also shown that the improvement in breathing rate is enhanced in the CCHS group with disturbed breathing during sleep.

Experiments were conducted to examine the effect of limb stimulation on the breathing rate of subjects with congenital central hypoventilation (CCHS). FIG. 11 shows the increase in breathing rate accompanying three periods of foot movement (indicated by shaded areas) in 30 normal subjects (control) and 15 children diagnosed with congenital central hypoventilation syndrome. Foot movement substantially increased breathing rate, and much more so in the patients than in normal subjects.

The purpose of this experiment was to demonstrate the basic tenet of the present method, that nerve signals from foot movement enhance breathing, and is particularly effective in particular patients with breathing disorders. Respiratory movements were recorded by an air-filled bag held in place with a belt on the thoracic wall; a non-compliant tube lead from the bag to a pressure transducer. All physiologic signals were recorded on a laptop data acquisition system (InstruNet; GW Instruments, Somerville Mass., USA). The respiratory signal was sampled at 100 Hz. Passive foot motion was induced by investigator-initiated manual extension/flexion at 23 flexions/min. The leg was raised at the calf so that the movement occurred at the ankle, with flexion and extension of the foot being maximal and consistent. The rate of 23 flexions/min was chosen as sufficiently rapid to facilitate breathing, while still being comfortable for the subject. Movements were performed by a researcher who maintained foot contact for the entire period to minimize novel sensory responses. The same procedure was then repeated for the opposite foot; initial selection of left or right foot was random. Respiratory and heart rates were derived from the peak-to-peak intervals in recorded signals. Breathing rates were calculated from the thoracic movement signal. The mean rates were calculated for all subjects across the three periods of passive foot movements, and displayed with inter-subject standard errors across the entire period. The data show that respiratory rates increased during periods of foot movements in control subjects, and increased more for congenital central hypoventilation subjects. Those data provide evidence that nerve signals from foot movement can enhance breathing rates.

Figure 14A:
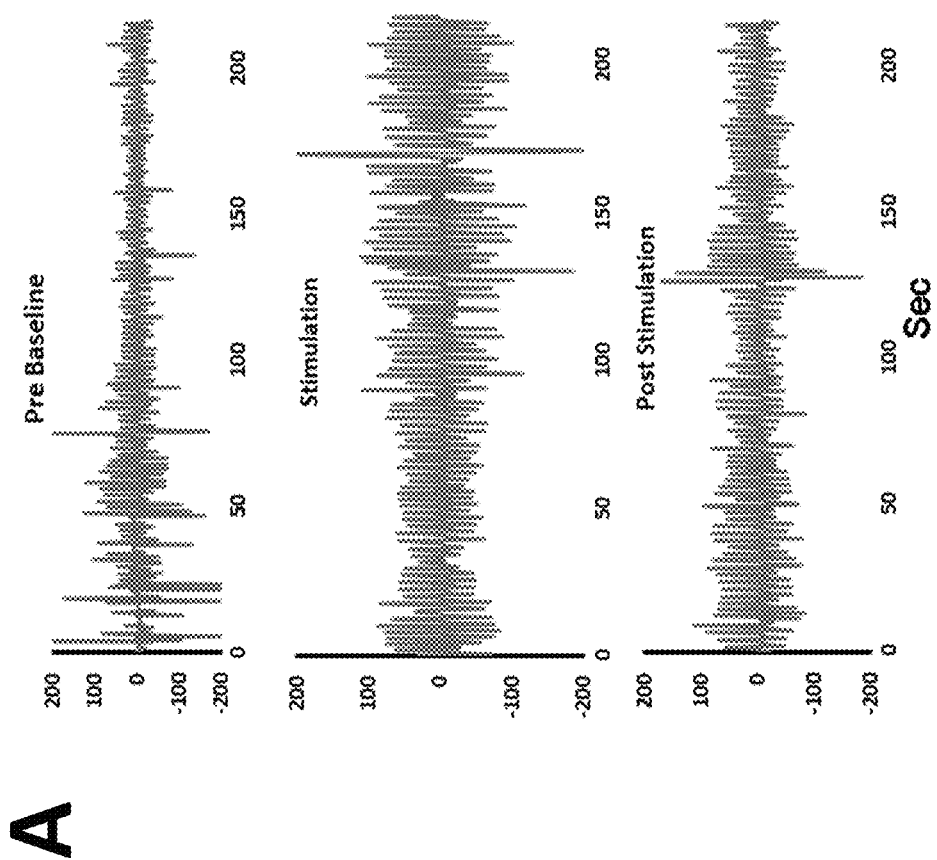
FIG. 14A through FIG. 14C, depicts the results of an experiment examining the effect of stimulation of the hand on a patient with congenital central hypoventilation.
Figures 14B, 14C:
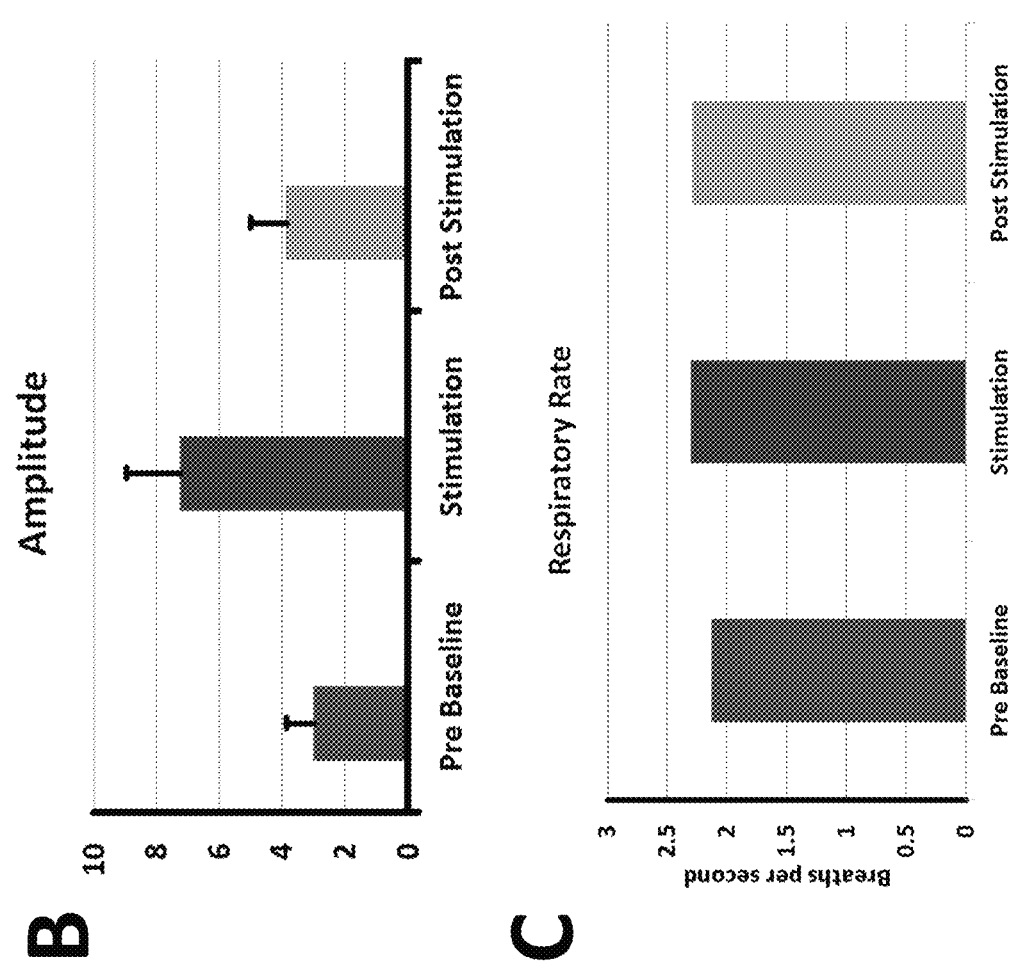

An experiment was conducted examining the effect of vibrational stimulation of the hand on the respiration of a subject with CCHS. Respiratory tracings (airflow) from Pre (Baseline), Stimulation on hand, and Post Stimulation periods from a 2 year old congenital central hypoventilation patient under clinical intervention is shown in FIG. 14A. It was observed that stimulation significantly enhanced amplitude, without changing the respiratory rate (FIG. 14B and FIG. 14C).

Example 2: Respiratory Analysis of Subjects Before and after Stimulation

Experiments were conducted to examine the effects of limb stimulation on the respiration of breathing-impaired subjects. The subjects were two young adult patients with severe spinal injury at upper thoracic levels at least 1 year post-trauma. Subjects were instrumented with thoracic wall and abdominal excursion sensors, oxygen saturation sensors, electroencephalographic, eye movement, and electrocardiograph leads (3 lead ECG) (SomnoMedics Inc; Fla.) for recording of physiological measures and assessment of sleep state, and recorded for two consecutive nights. Vibration devices were placed on the palms of the left hand, and parameters were set at continuous vibration with pulse durations of 0.4 sec, inter-pulse duration of 0.4 sec, and continued for 460 min. FIG. 12A and FIG. 12B show numerical values for respiratory measures from subject 1 and subject 2, respectively. FIG. 12C demonstrates that the respiratory disturbance index (RDI) decreased for the two studied subjects during stimulation. For example, subject 1 had an RDI of 67.4 on night 1 (before stimulation) and 18.2 on night 2 (during stimulation). Subject 2 had an RDI of 23.3 on night 1 (before stimulation) and 6.3 on night 2 (during stimulation).

Example 3: Sleep Stages

Figure 13A:
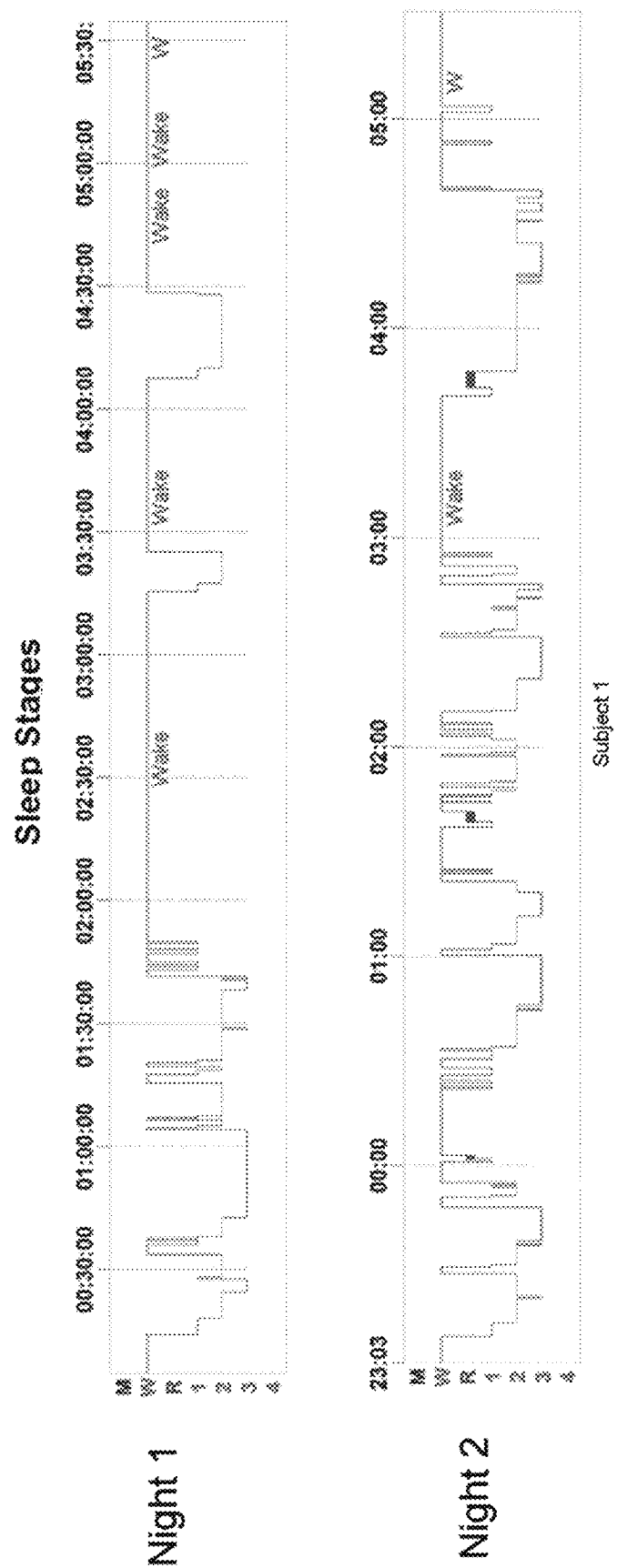
FIG. 13A and FIG. 13B, depicts the results of an experiment examining the effect of limb stimulation on the integrity of sleep stages from two different subjects, where stimulation was induced on night two of each subject.
Figure 13B:
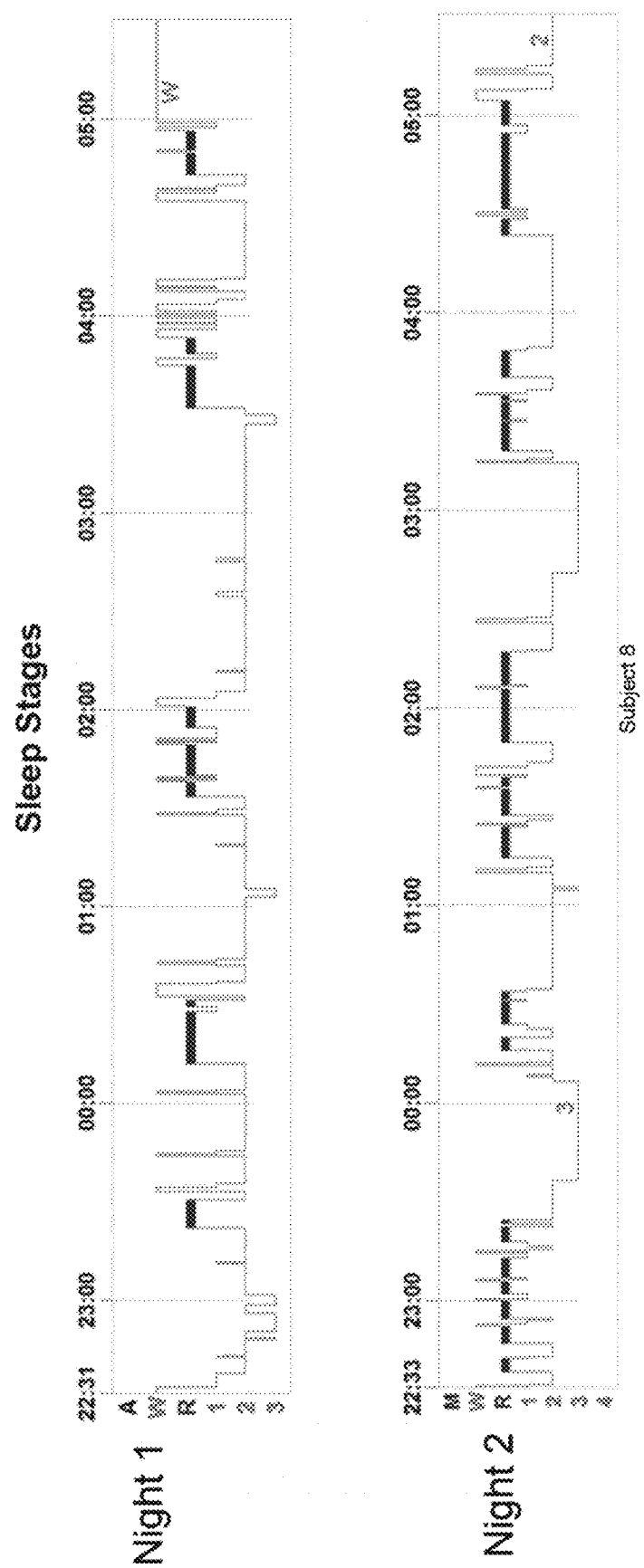

Experiments were conducted to examine the effects of limb stimulation on the sleep stages of subjects. FIG. 13A and FIG. 13B depict the sleep stages of a two subjects on nights 1 and 2. These studies were carried out concurrently with the respiratory measures on the same spinal cord patients described above in Example 2, i.e., thoracic-level spinal injury young adults, with the same vibrator placement and stimulation parameters and length of recording. The thoracic and abdominal measures of breathing, electrocardiographic, oxygen saturation and electroencephalographic signals were collected by a Somnomedics acquisition system, and analyzed by Somnomedics software to determine sleep states. Minute-by-minute determination of sleep states were calculated and displayed (FIG. 13A and FIG. 13B). It is demonstrated that the sustained periods of waking when the subject should be sleeping was reduced in Night 2 (FIG. 13A). Further, stimulation induced much longer periods of rapid eye movement sleep (REM sleep) in the second night with stimulation (FIG. 13B). The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The invention claimed is:

1. A method for increasing air intake by a subject and improving sleep state integrity, comprising:
   positioning at least one vibrator on at least one limb of a subject;
   generating a stimulus signal indicative of a proprioceptor nerve response from limb motion during walking or running; and
   stimulating proprioceptive afferent nerve fibers in the at least one limb via vibrational motion delivered by the at least one vibrator and driven by the stimulus signal, whereby the stimulated nerves interact with the subject's brain to reflexively increase air intake by the subject and improve sleep state integrity.

2. The method of claim 1, wherein the at least one limb is the subject's foot.

3. The method of claim 1, wherein the at least one limb is the subject's hand.

4. The method of claim 3, wherein the stimulated nerves are the median and ulnar nerves.

5. The method of claim 1, wherein the at least one vibrator is controlled by a control unit.

6. The method of claim 5, wherein the control unit is programmable.

7. The method of claim 6, wherein the control unit is programmable via a computing device wired or wirelessly connected to the control unit.

8. The method of claim 5, wherein the control unit controls the at least one vibrator wirelessly.

9. The method of claim 1, wherein the subject is sleeping.

10. The method of claim 1, wherein stimulating the nerve comprises delivery of pulses via the at least one vibrator, where the pulses are delivered at a rate of about 20-150 Hz.

11. The method of claim 10, wherein the delivery of pulses is repeated.

12. The method of claim 1, wherein the subject has a condition selected from the group consisting of hypoventilation, obstructive sleep apnea, heart failure, central sleep apnea, apnea of prematurity, apnea of infancy, muscular dystrophy, spinal cord injury, and stroke.

13. A system for enhancing the breathing of a subject to improve sleep state integrity, comprising:
- at least one vibration motor;
- a control unit communicatively connected to the at least one vibration motor and configured to generate a stimulus signal indicative of proprioceptor nerve responses from limb motion during walking or running; and
- a means for securing the at least one vibration motor to at least one limb of a subject;
- wherein the control unit is configured to initiate the stimulus signal to the at least one vibration motor to generate vibrational motion to the at least one limb of the subject, such that the vibrational motion stimulates proprioceptive afferent nerve fibers in the at least one limb to elicit an enhanced breathing effort by the subject to improve sleep state integrity.

14. The system of claim 13, wherein the control unit is programmable.

15. The system of claim 13, wherein the control unit controls the vibration motor wirelessly.

16. The system of claim 14, wherein the at least one vibration motor is programmed to vary inputs from the group selected from the pulse rate, pulse duration, interpulse duration, burst duration, interburst duration, and pulse amplitude.

17. The system of claim 14, wherein the at least one vibration motor is programmed to pulse in a variable-amplitude sequence.

18. The system of claim 13, wherein the at least one vibration motor is between 2-15 mm in diameter.

19. The system of claim 13, wherein the means for securing the at least one vibration motor to at least one limb of a subject comprises embedding the at least one vibration motor in a material attached to the subject's limb.

20. The system of claim 13, wherein the means for securing the at least one vibration motor to at least one limb of a subject comprises positioning the vibration motor against the skin surface of the subject's limb and covering the vibration motor with a material attached to the subject's limb.

* * * * *